US00PP28938P3

(12) United States Plant Patent
Ranney

(10) Patent No.: US PP28,938 P3
(45) Date of Patent: Feb. 6, 2018

(54) ***ILEX* PLANT NAMED 'NCIV2'**

(50) Latin Name: *Ilex verticillata*
Varietal Denomination: NCIV2

(71) Applicant: North Carolina State University, Raleigh, NC (US)

(72) Inventor: Thomas Green Ranney, Arden, NC (US)

(73) Assignee: North Carollna State University, Raleigh, NC (US)

( * ) Notice: Subject to any disclaimer, the term of this patent is extended or adjusted under 35 U.S.C. 154(b) by 0 days.

(21) Appl. No.: 14/999,195

(22) Filed: Apr. 7, 2016

(65) Prior Publication Data

US 2017/0295687 P1 Oct. 12, 2017

(51) Int. Cl.
*A01H 5/12* (2006.01)

(52) U.S. Cl.
USPC ..... Plt./247

(58) Field of Classification Search
USPC ..... Plt./247
See application file for complete search history.

*Primary Examiner* — Keith O Robinson
(74) *Attorney, Agent, or Firm* — Cassandra Bright

(57) ABSTRACT

'NCIV2' is a new tetraploid cultivar of deciduous holly with a compact, roughly rounded growth habit, and prolific, large, showy orange fruit.

1 Drawing Sheet

Latin name of the genus and species: The Latin name of the novel plant variety disclosed herein is *Ilex verticillata.*

Variety denomination: The inventive seedling selection of *Ilex verticillata* disclosed herein has been given the varietal denomination 'NCIV2'.

BACKGROUND OF THE INVENTION

The present invention comprises a new and distinct winterberry holly cultivar hereinafter referred to by the cultivar name 'NCIV2'. This new holly was developed at North Carolina State University, Mills River, N.C. 'NCIV2' was selected from a population of seedlings grown from an open-pollinated selection of *Ilex verticillata* (NCSU 1998-538, unpatented, parentage unknown). 'NCIV2' was selected based on its compact form and prolific, large, orange, showy fruit. DNA content of 'NCIV2' was determined using flow cytometry and found to be approximately twice that of *I. verticillata* 'Winter Red' (unpatented) indicating that 'NCIV2' is a natural tetraploid.

The first asexual propagation of 'NCIV2' was carried out in July 2008 by rooting stem cuttings at the North Carolina State University, Mountain Horticultural Crops Research Station, Mills River, N.C. and has been asexually reproduced repeatedly by vegetative cuttings over a 7 year period. 'NCIV2' roots readily from softwood cuttings treated with a basal dip of 2,500-5,000 ppm indole butyric acid (potassium salt) in water. 'NCIV2' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Compact habit and small stature.
2. Prolific, large, orange fruit.

3. 2C DNA content of approximately 4.15 pg indicating it is a tetraploid cytotype.

BRIEF DESCRIPTION OF THE DRAWING

This new holly is illustrated by the accompanying photograph which shows the plant's form and fruit characteristics. The colors shown are as true as can be reasonably obtained by conventional photographic procedures. Colors in the photograph may differ slightly from the color values cited in the detailed botanical description, which accurately describe the colors of the new hybrid holly.

FIG. 1 is a color photograph showing the form and fruit of 'NCIV2' in early spring 2014 on an eight-year-old plant in Mills River, N.C.

DETAILED BOTANICAL DESCRIPTION

The following is a detailed description of the botanical characteristics of the new and distinct holly variety known by the denomination 'NCIV2'. The detailed description was taken on an eight-year-old field-grown plant in Mills River, N.C. in 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Ilex verticillata* 'NCIV2'.

*Common name.*—Winterberry holly.

Parentage: Seedling grown from an open-pollinated selection of *Ilex verticillata*, NCSU 1998-538 (unpatented).

Plant description:

*Growth habit.*—Deciduous shrub. Compact, rounded/oval in shape.

*Height*.—About 90 cm after nine years.
*Width*.—About 100 cm after nine years.

Shoot and stem:
*Mature stem texture*.—Finely pubescent, with lenticels.
*Mature stem color*.—Brown (197B) with brown (N200D) lenticels.

Lateral branches:
*Length*.—About 13.5 cm.
*Diameter*.—About 2 mm.
*Internode length*.—About 3.3 cm.
*Strength*.—Strong.
*Texture*.—Smooth, glabrous.
*Color*.—Immature: Green (138A). Mature: Grayed-green (198A).
*Lenticels*.—Length: About 1 mm. Diameter: About 1 mm. Color: Grey-brown (199C) to grey-brown (199D).

Roots: Fibrous, freely branching.

Leaves:
*Arrangement*.—Alternate, single.
*Length*.—Avg. 5.15 cm (3.1 to 7.2 cm).
*Width*.—Avg. 2.75 cm (0.8 to 4.7 cm).
*Leaves per lateral branch*.—100 to 200.
*Shape*.—Elliptic.
*Apex*.—Apiculate.
*Base*.—Attenuate.
*Margin*.—Serrulate.
*Fragrance*.—None.
*Aspect*.—Flat.
*Venation pattern*.—Pinnate.
*Texture*.—Upper Surface: Smooth, glabrous. Lower Surface: Pubescent, slightly rugose.
*Emerging leaves*.—Color: Upper: Green (144A). Lower: Yellow-green (144A).
*Mature leaves during growing season*.—Color: Upper: Green (139A). Lower: Green (147B).
*Venation*.—Upper Surface: Green (145C). Lower Surface: Yellow-green (145C).
*Petiole*.—Length: Avg. 1.1 cm (0.5 to 1.6 cm). Diameter: Avg. 0.68 mm (0.36 to 0.99 mm). Texture: Upper: Glabrous. Lower: Glabrous. Color: Upper: Yellow-green (145C). Lower: Yellow-green (145C).
*Leaf bud*.—Length: 1 mm. Diameter: 1 mm. Texture: Slightly rough.
*Stipules*.—Not present.

Inflorescence:
*Description*.—Small, axillary cup-shaped flowers, solitary. Flowers face upright to outward. Flowers not persistent.
*Number of true flowers per inflorescence*.—1.
*Flowering season*.—Summer; June and July in Mills River, N.C.
*Fragrance*.—None detected.
*Bud*.—Shape: Globular. Length: About 2 mm. Diameter: About 2 mm. Color: Green-white (157A).
*Flower*.—Diameter: 1 mm. Length: 1 mm.
*Petals*.—Arrangement: Whorl. Number: 7. Fused: Not fused. Texture: Smooth. Shape: Oblong. Margin: Entire. Apex: Rounded. Base: Attenuate. Length: About 3 mm. Width: About 2.0 mm. Texture: Upper: Smooth, glabrous. Lower: Smooth, glabrous. Color when opening: Upper: White (157B). Lower: White (157A). Color at anthesis: Upper: Green-white (157B). Lower: Green-white (157A).
*Sepal*.—Quantity per flower: 7. Length: About 1.5 mm. Width: About 1 mm. Shape: Deltoid. Apex: Acute. Base: Fused. Margin: Entire. Texture: Upper: Smooth, glabrous. Lower: Smooth, glabrous. Color: Upper: Yellow-green (144A). Lower: Yellow-green (144A).
*Peduncle*.—Length: About 2 mm. Diameter: About 1.0 mm. Orientation: About 20 to 40 degrees from vertical. Strength: Strong. Color: Yellow-green (144A).

Reproductive traits:
*Sex*.—Functional female (dioecious). Needs male pollinator to fertilize.
*Gynoecium*.—Pistil number: 1. Pistil length: About 7 mm. Stigma shape: Oblong. Stigma color: Yellow-green (144A). Ovary shape: Oval. Ovary color: Green (143A).
*Androcoecium*.—Stamen number: 7. Anther shape: Narrowly deltoid. Anther attachment: Basifixed. Anther size: About 1.0 mm long and 0.5 mm wide. Anther color: Green-white (157D). Amount of pollen: None observed.

Fruit and seed:
*Fruit type*.—Drupe.
*Fruit texture*.—Smooth, glabrous.
*Fruit quantity per flower*.—1.
*Fruit shape*.—Spherical, somewhat flattened.
*Fruit diameter*.—Avg. 8.71 mm (7.38 to 10.04 mm). Fruit Length: 7.1 to 10 mm.
*Fruit color*.—Immature: Yellow-Green (145A). Mature: Orange-Red (33B).
*Days to ripening*.—About 75.
*Longevity on plant*.—More than 2 weeks.
*Seed number*.—About 7.
*Seed length*.—Avg. 4.9 mm (4.17 mm to 5.56 mm).
*Seed diameter*.—Avg. 2.36 mm (1.75 to 2.96 mm).
*Seed shape*.—Oblong to slightly crescent.
*Seed texture*.—Smooth, glabrous.
*Seed color*.—Yellow-Orange (44A).

DNA content: 2C DNA contend was determined following the methods of Shearer and Ranney (2013) using 4', 6-diamidino-2-phenylindole (DAPI) fluorochrome stain and *Pisum sativum* 'Ctirad' (unpatented) as an internal standard with 3 replications. Mean 2C DNA content for 'NCIV2' was 4.15±0.13 (SEM) pg, approximately twice the value of *I. verticillata* 'Winter Red' with a DNA content of 1.93±0.05 (SEM) pg indicating that 'NCIV2' is a tetraploid.

Disease and insect resistance: No significant disease or insect pests have been observed.

Cold hardiness: At least USDA zone 5; testing has not been completed in colder zones.

COMPARISON WITH OTHER CULTIVARS

Table 1 shows comparison of distinguishing characteristics between *Ilex verticillata* 'NCIV2', the female parent (NCSU 1998-538), and cultivars 'NCIV1' and 'Winter Red' (U.S. Plant Pat. No. 4,146). 'NCIV2' is distinguished from *Ilex verticillata* 'Winter Red' by having twice the genomic DNA content indicating it is a tetraploid and having a smaller, compact stature, and larger diameter orange fruit. 'NCIV2' is distinguished from both 'NCIV1' and NCSU 1998-538 with its distinct orange-red fruit.

TABLE 1

Comparison of *Ilex verticillata* taxa.

| Trait | Taxa: Ilex verticillata 'Winter Red' | Ilex verticillata NCSU 1998-538 | Ilex verticillata 'NCIV1' (U.S. Plant Pat. No. 27,109) | Ilex verticillata 'NCIV2' |
|---|---|---|---|---|
| Plant height & diameter | About 96 in. × 96 in. | About 50 in. × 50 in. | About 40 in. × 40 in. | About 36 in. × 40 in. |
| Plant habit | Erect, rounded shape | Rounded | Compact, roughly rounded shape | Compact, roughly rounded shape |
| Fruit diameter (mm) | Mean: 6 Range: 4 to 8 | Mean: 8 Range: 6 to 10 | Mean: 10 Range: 8 to 12 | Mean: 8.71 Range: 7.38 to 10.04 |
| Fruit color | Reddish-orange (40B) | Reddish-orange (40C) | Red (44A/B) | Orange-red (33B) |

TABLE 1-continued

Comparison of *Ilex verticillata* taxa.

| Trait | Taxa: Ilex verticillata 'Winter Red' | Ilex verticillata NCSU 1998-538 | Ilex verticillata 'NCIV1' (U.S. Plant Pat. No. 27,109) | Ilex verticillata 'NCIV2' |
|---|---|---|---|---|
| DNA content (pg) mean ± SEM | 1.93 ± 0.05 | 4.33 ± 0.05 | 4.38 ± 0.03 | 4.15 ± 0.13 |
| Estimated ploidy level | Diploid | Tetraploid | Tetraploid | Tetraploid |

What is claimed is:

1. A new and distinct hybrid holly plant named 'NCIV2' substantially as illustrated and described herein.

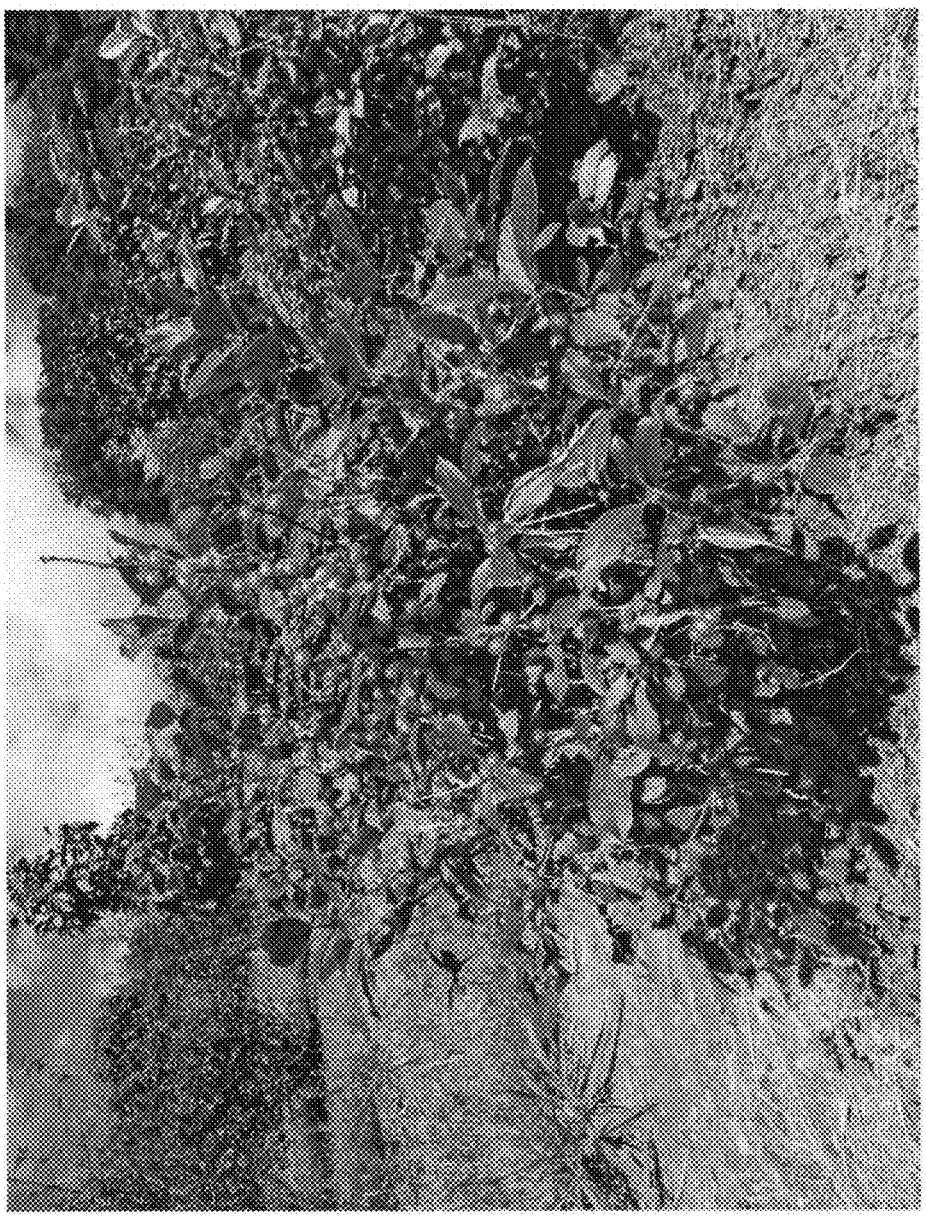

* * * * *